United States Patent
Curry et al.

(10) Patent No.: US 8,178,756 B2
(45) Date of Patent: May 15, 2012

(54) THIN-SKINNED CHILE PEPPER VARIETY

(75) Inventors: Edward N. Curry, Pearce, AZ (US); Philip L. Villa, Camarillo, CA (US)

(73) Assignee: Curry Seed & Chili Co., Pearce, AZ (US)

( * ) Notice: Subject to any disclaimer, the term of this patent is extended or adjusted under 35 U.S.C. 154(b) by 453 days.

(21) Appl. No.: 12/366,507

(22) Filed: Feb. 5, 2009

(65) Prior Publication Data

US 2010/0199392 A1 Aug. 5, 2010

(51) Int. Cl.
*A01H 5/00* (2006.01)
*A01H 5/08* (2006.01)
*A01H 5/10* (2006.01)

(52) U.S. Cl. ................................ 800/317.1; 800/265

(58) Field of Classification Search ........................ None
See application file for complete search history.

(56) References Cited

U.S. PATENT DOCUMENTS

| | | | | |
|---|---|---|---|---|
| 4,208,435 | A | * | 6/1980 | Wood .............................. 426/92 |
| 5,262,316 | A | * | 11/1993 | Engler et al. .................. 800/294 |
| 6,143,349 | A | | 11/2000 | Arevalos et al. |
| 7,087,819 | B2 | | 8/2006 | Edwards |
| 2002/0007502 | A1 | | 1/2002 | Nash |
| 2005/0055743 | A1 | | 3/2005 | Nicolet et al. |

FOREIGN PATENT DOCUMENTS

WO WO-98/28430 * 7/1998

OTHER PUBLICATIONS

Cheema et al. The Indian Journal of Horticulture 2(2): 49-61 (Dec. 1944).*
PI 268106 (Sandia) deposited 1960.*
PI 586666 (Anaheim) deposited 1962.*
International Search Report and Written Opinion, mailed Mar. 30, 2010, PCT/US10/22861.
Lippert et al. "New Pepper Varieties" California Agriculture 21(12):v021, n12, p. 10. Dec. 1-20, 1967 (available online at <http://ucce.ucdavis.edu/liles/repositoryfiles/ca2112p1 0-64379.pdf> ).
Coon et al. The Chile Cultivars of New Mexico State University Released from 1913 to 2008. 1-20, New Mexico State university. Agricultural Experiment Station, College of Agriculture and Home Economics, Nov. 2008, p. 1-8. (available online at <http://aces.nmsu.edu/pubs/research/horticulture/RR-763.pdf) p. 1, p. 3.

* cited by examiner

*Primary Examiner* — David T Fox
(74) *Attorney, Agent, or Firm* — Quarles & Brady LLP; Gavin J. Mllczarek-Desai

(57) ABSTRACT

An improved Anaheim-type chile pepper cultivar having a fruit characterized by a relatively thin skin in comparison to other Anaheim-type chile pepper cultivars, such that mechanized peeling of fruit results in an average recovery, excluding skin, seed, and placenta, that is at least 5% higher in comparison to the peeling of an existing Anaheim-type chile pepper cultivar. The improved cultivar further is characterized by a mature seed content of less than 20 pounds per 1000 pounds of fruit and by fruit that is readily de-stemmed by mechanized de-stemming.

3 Claims, 1 Drawing Sheet

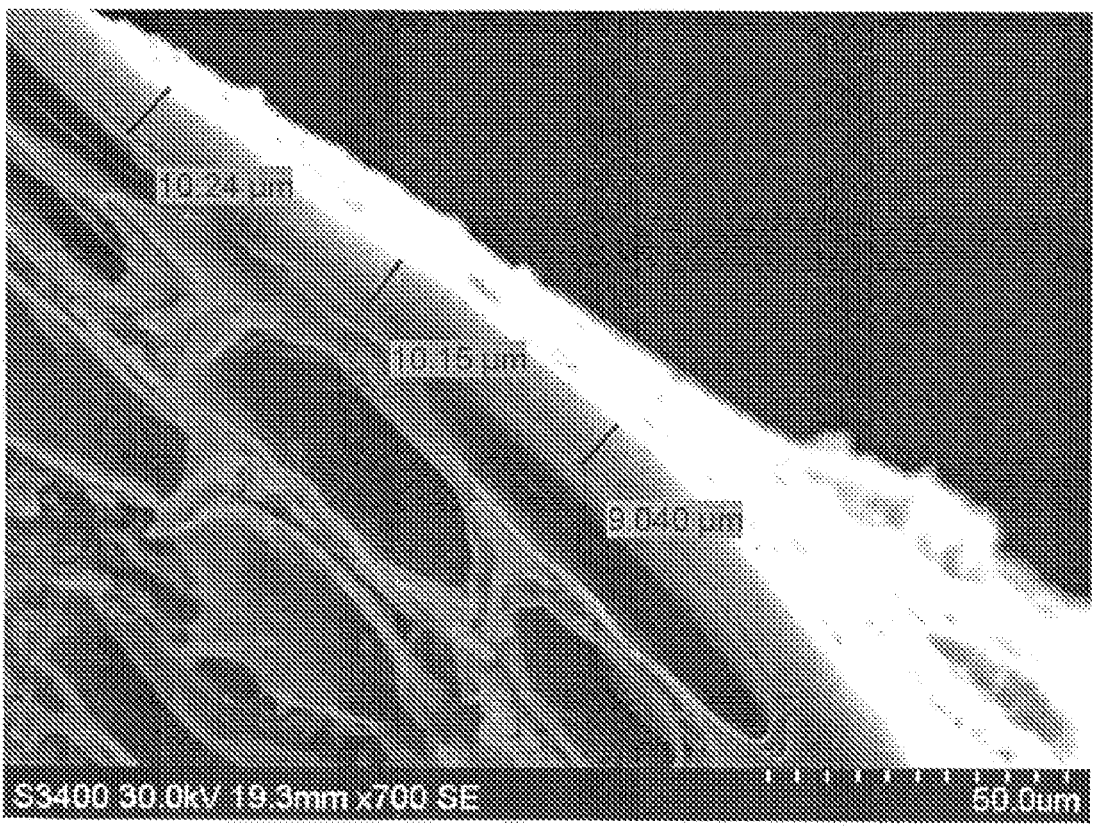
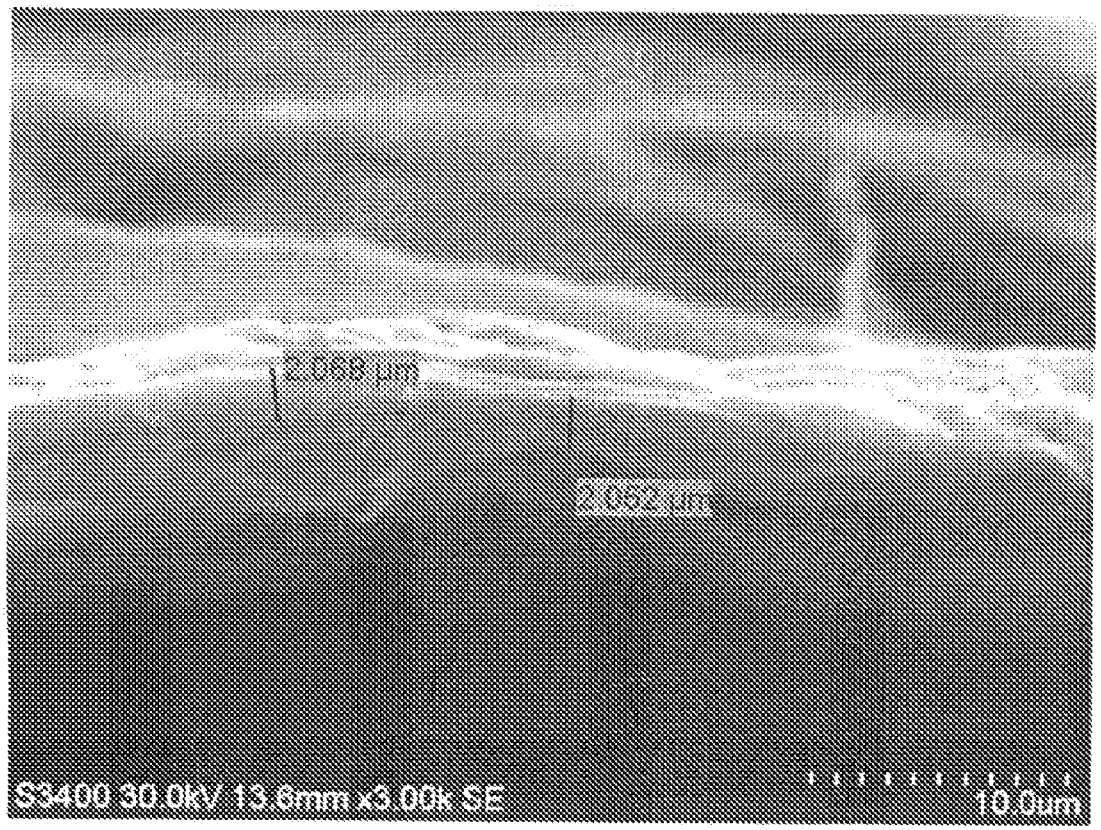

THIN-SKINNED CHILE PEPPER VARIETY

FIELD OF THE INVENTION

The invention relates to a novel variety of Anaheim-type chile pepper that results in a fruit that is thin-skinned in terms of being readily peeled and lower in mature seed content compared to other Anaheim-type varieties in pepper cultivars of the genus Capsicum.

BACKGROUND OF THE INVENTION

Within the genus *Capsicum*, the species *Capsicum annuum* L. cultivars possess a range of pod shapes and colors complemented by varying degrees seed content, skin thickness, and flavor intensity. Each cultivar has a "heat" or pungency that ranges from mild to hot. The pungent active ingredient found in peppers is the aromatic phenol capsaicin, which is produced by oil secreting glands located along the placenta. Thus, pepper varieties having smaller placenta content typically are milder in flavor.

The commercial value of chile peppers lies in the recovery of the flesh (which excludes seeds, skin, and placenta) and is the raw material for several chile-pepper consumer products, and in the seeds, which are sold to agricultural producers of the fruit. Thus, the commercial processing of chile peppers necessarily involves the separation of flesh and seeds from the rest of the fruit (skin and placenta) and from other materials (such as the stem and calyx) that may be collected during harvesting of the pepper.

Attempts have been made to harvest peppers by machine and then to separate the flesh and seeds from the rest of the fruit using flotation and/or pneumatic equipment, but these experiments have not been consistently successful. Moreover, commercial peeling operations often rely on roasting and/or steam to separate the skin from the cell wall of the fruit. Due to the thickness of the skin, processing of typical Anaheim-type chile cultivars results in a flesh recovery of about 70% by weight of each pepper fruit. Moreover, the processing of Anaheim-type chile peppers (and other varieties) often is time, labor, and/or resource intensive due to the amount of energy used to roast or steam peel.

Thus, it would be desirable for a solution to the problem associated with the high cost of processing chile peppers due to excessive skin thickness and to improve the flesh recovery percentage associated with processing.

SUMMARY OF THE INVENTION

The present invention relates to *Capsicum annuum* seeds and plants or varieties ("cultivars") that produce fruit (i.e., peppers) that is characterized by a skin that is thinner in comparison to existing Anaheim-type chile pepper cultivars.

More specifically, the invention relates to an Anaheim-type chile cultivar in which the skin weighs at least 10% less than that of an existing Anaheim-type chile pepper cultivar and has an average skin thickness that is at least 10% thinner than an existing Anaheim-type chile pepper cultivar, with the improved variety skin averaging between 2-3 micrometers in thickness compared to 8 microns or more for comparison Anaheim varieties. The thinness of the improved varieties skin has been found to result in an average recovery, excluding skin, seed, and placenta, that is at least 5% higher in comparison to standard mechanized peeling of an existing Anaheim-type chile pepper cultivar.

The invention further relates to an Anaheim-type chile cultivar characterized in that mechanized de-stemming results in stem and calyx removal a high percentage of the time, typically at least 98 of 100 fruit.

The invention also relates to an Anaheim-type chile cultivar having fruit that is characterized by a mature seed content of at least 10% less than that of an existing Anaheim-type chile pepper cultivar. Preferably, the mature seed content is less than 20 pounds per 1000 pounds of fruit.

Moreover, the invention relates to an Anaheim-type chile cultivar having fruit that weighs on average at least 60 grams and has a wall thickness of at least 0.10 inches.

Various other purposes and advantages of the invention will become clear from its description in the specification that follows. Therefore, to the accomplishment of the objectives described above, this invention includes the features hereinafter fully described in the detailed description of the preferred embodiments, and particularly pointed out in the claims. However, such description discloses only some of the various ways in which the invention may be practiced.

BRIEF DESCRIPTION OF THE FIGURES

FIG. 1 shows a comparison of the skin thickness between an existing Anaheim-type chile variety and a cultivar of the present invention.

DETAILED DESCRIPTION OF THE INVENTION

Pedigree Synopsis for Anaheim-Type Chile Pepper Cultivar Villa 96

The basic parents of the Villa 96 cultivar are the San Martin Ancho F2 Line and Breeding Line 17 (an Anaheim-type long green chile pepper). The above Lines were crossed using standard Mendalian genetics and eight generations were grown under typical chile growing conditions in Pearce, Ariz. Field selections were performed based on thick wall (making the fruit heavier, with an average weight of at least 60 grams), and Anaheim-type characteristics, such as fruit with 2.5 inch width and 6-8 inch length, a tapered end, easy de-stem ability, rounded shoulders, smooth fruit and mild heat (typically about 50 Scoville units), heavy fruiting plant habit, and observations of bacteria spot (Xanthomonas, common leaf spot) tolerance. It was discovered that the skin of improved cultivar was more readily peeled than other Anaheim-type varieties.

Subsequent testing confirmed a thin-skin phenotype as shown in the electron micrograph images in FIG. 1. The top panel shows the skin thickness of an Anaheim-type chile comparison variety, while the lower panel shows the skin thickness of the improved cultivar of the invention. As described in the FIGURE and in Table 1 below, the average thickness of skin for the improved cultivar was 2.85 micrometers, with 7/8 samples measuring between 2 and 3 micrometers. In comparison, the other Anaheim-type cultivar had a skin thickness that averages 9.69 micrometers. Thus, the skin of the improved cultivar has an average thickness that is at least 10% thinner than existing Anaheim-type chile pepper cultivars and preferably is at least 20% thinner.

TABLE 1

| Thin skin peppers | Reference peppers |
|---|---|
| 2.119 | 9.229 |
| 2.614 | 9.696 |
| 2.424 | 9.165 |
| 7.304 | 10.68 |
| 2.068 | 10.24 |
| 2.052 | 10.15 |
| 1.996 | 9.04 |

TABLE 1-continued

| Thin skin peppers | Reference peppers | |
|---|---|---|
| 2.223 | 9.329 | |
| 2.85 | 9.691125 | Average thickness in um. |

Improved cultivars of the invention have been tested for ease of peeling under standard conditions for such processing by chile canners and other food companies. The results from tests done by a processing facility in New Mexico indicate that the peppers of the Villa 96 variety were peeled on average 95% of the time as compared to 52% (average) of the time for a very commonly used Anaheim-type long green cultivars used under similar circumstances and undergoing the evaluation for peel effectiveness at the same point in the process.

Indeed, such peel evaluations have been performed on several long green peppers that are processed by the New Mexico facility mentioned above. Strict methods were used to define a "peeled pepper" and applied to all of the peppers that were evaluated. In each case, the data indicated that the effectiveness of peel removal for the Villa 96 cultivar was on average 95% as compared to 52% for the commonly processed long green cultivars.

Testing by another company has revealed that the fruit of the improved cultivar has an average wall thickness of at least 0.10 inches. Moreover, ten mechanized peeling trials of fruit of the improved cultivar resulted in an average recovery of flesh, i.e., excluding skin, seed, and placenta, that is at least 5% higher in comparison to the peeling of an existing Anaheim-type chile pepper cultivar, New Mexico 6-4.

The ten trials described above also revealed that the skin of the improved cultivar weights at least 10% less than that of the existing Anaheim-type chile pepper cultivar New Mexico 6-4 (an average of 4.6% of the improved cultivar's weight was peel (i.e., skin) compared with an average of 7.75% peel by weight of New Mexico 6-4).

Thus, an Anaheim-type chile pepper cultivar of the invention has a fruit that is characterized by a skin that is thinner in comparison to existing Anaheim-type chile pepper cultivars.

The Anaheim-type chile pepper cultivar of the invention has been found to have a fruit characterized by a mature seed content of at least 10% less by weight than that of all existing Anaheim-type chile pepper cultivars with which it has been compared. For example, the improved cultivar has been found to contain a mature seed content that is less than 20 pounds per 1000 pounds of fruit. Other Anaheim-type cultivars typically contain approximately at least 25 pounds of mature seed per 1000 pounds of fruit.

Moreover, the improved cultivar is further characterized by easy de-stemming, in that mechanized de-stemming results in stem and calyx removal in at least 98 of 100 of fruit.

Deposit Information

Two thousand five hundred (2500) seeds of Anaheim-type Villa 96 Chile cultivar that produces thin-skinned fruit have been placed on deposit with the American Type Culture Collection (ATCC), 10801 University Blvd., Manassas, Va., 20110-2209 under Patent Deposit Designation Number PTA-9751 on Feb. 2, 2009. This deposit was made in compliance with the Budapest Treaty requirements that the duration of the deposit should be for thirty (30) years from the date of deposit or for five (5) years after the last request for the deposit at the depository or for the enforceable life of a U.S. Patent that matures from this application, whichever is longer. These *Capsicum annuum* seeds will be replenished should it become non-viable at the depository.

Plants and fruit resulting from the deposited seed have been grown in Southern Arizona and found to exhibit the thin-skin phenotype and other characteristics described herein.

The Anaheim-type chile cultivars of the present invention are genetically stable. Nonetheless, the characteristics described herein may be adversely affected by environmental factors (such as high temperatures, low soil fertility, or water stress) and may vary in fruit from plant to plant, while still maintaining a thin-skinned phenotype that is easier to peel in comparison to all other Anaheim-type chile varieties.

Various changes in the details and components that have been described may be made by those skilled in the art within the principles and scope of the invention herein described in the specification and defined in the appended claims. Therefore, while the present invention has been shown and described herein in what is believed to be the most practical and preferred embodiments, it is recognized that departures can be made therefrom within the scope of the invention, which is not to be limited to the details disclosed herein but is to be accorded the full scope of the claims so as to embrace any and all equivalent processes and products.

What is claimed is:

1. An Anaheim-type chile pepper seed from a cultivar of the Villa 96 line, representative seed of said line having been deposited under ATCC Patent Deposit Designation No. PTA-9751.

2. A plant produced from the seed of claim 1.

3. A fruit resulting from a plant produced from the seed of claim 1.

* * * * *